(12) United States Patent
Locklin (10) Patent No.: US 9,315,628 B2
(45) Date of Patent: Apr. 19, 2016

(54) PERMANENT ATTACHMENT OF AGENTS TO SURFACES CONTAINING C-H FUNCTIONALITY

(75) Inventor: Jason J. Locklin, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/124,045

(22) PCT Filed: Jul. 12, 2012

(86) PCT No.: PCT/US2012/046400
§ 371 (c)(1),
(2), (4) Date: Dec. 5, 2013

(87) PCT Pub. No.: WO2013/012664
PCT Pub. Date: Jan. 24, 2013

(65) Prior Publication Data
US 2014/0121333 A1     May 1, 2014

Related U.S. Application Data (60) Provisional application No. 61/508,438, filed on Jul. 15, 2011.

(51) Int. Cl.
| | | |
|---|---|---|
| C08G 69/48 | (2006.01) |
| C08G 63/00 | (2006.01) |
| C08B 15/00 | (2006.01) |
| D06M 13/127 | (2006.01) |
| A61Q 5/10 | (2006.01) |
| D06P 5/20 | (2006.01) |
| D06M 10/10 | (2006.01) |
| D06M 15/256 | (2006.01) |
| D06P 1/651 | (2006.01) |
| C09B 67/00 | (2006.01) |
| A61K 8/35 | (2006.01) |
| B05D 5/08 | (2006.01) |
| C08G 63/91 | (2006.01) |
| C09B 1/02 | (2006.01) |
| C09B 21/00 | (2006.01) |
| C09B 23/16 | (2006.01) |
| C09B 69/10 | (2006.01) |
| B05D 7/00 | (2006.01) |

(52) U.S. Cl.
CPC . *C08G 69/48* (2013.01); *A61K 8/35* (2013.01); *A61Q 5/10* (2013.01); *B05D 5/083* (2013.01); *C08B 15/00* (2013.01); *C08G 63/91* (2013.01); *C09B 1/02* (2013.01); *C09B 21/00* (2013.01); *C09B 23/166* (2013.01); *C09B 68/41* (2013.01); *C09B 68/46* (2013.01); *C09B 69/101* (2013.01); *C09B 69/103* (2013.01); *C09B 69/106* (2013.01); *C09B 69/109* (2013.01); *D06M 10/10* (2013.01); *D06M 13/127* (2013.01); *D06M 15/256* (2013.01); *D06P 1/65112* (2013.01); *D06P 5/2005* (2013.01); *B05D 7/54* (2013.01); *D06M 2400/01* (2013.01)

(58) Field of Classification Search
None
See application file for complete search history.

(56) References Cited

U.S. PATENT DOCUMENTS

| | | |
|---|---|---|
| 3,507,606 A | 4/1970 | Hildreth et al. |
| 3,697,402 A | 10/1972 | Clifton et al. |
| 5,354,341 A | 10/1994 | Moser et al. |
| 5,510,468 A | 4/1996 | Lamm et al. |
| 5,714,360 A | 2/1998 | Swan et al. |
| 6,558,158 B2 | 5/2003 | Yamaguchi |
| 7,709,544 B2 | 5/2010 | Doyle et al. |
| 8,114,319 B2 | 2/2012 | Davis et al. |
| 8,183,540 B2 | 5/2012 | Ward et al. |
| 2004/0182279 A1 | 9/2004 | Lee et al. |
| 2006/0105012 A1 | 5/2006 | Chinn et al. |
| 2006/0135639 A1 | 6/2006 | Singh |
| 2006/0147413 A1 | 7/2006 | Alferiev et al. |
| 2006/0148982 A1 | 7/2006 | Uchegbu et al. |
| 2007/0054119 A1 | 3/2007 | Garstecki et al. |
| 2007/0231291 A1 | 10/2007 | Huang et al. |
| 2008/0025503 A1 | 1/2008 | Choi et al. |
| 2009/0082553 A1* | 3/2009 | Satake et al. .................. 534/595 |
| 2009/0162767 A1 | 6/2009 | Wu |
| 2009/0196826 A1 | 8/2009 | Gao et al. |
| 2010/0136491 A1 | 6/2010 | Matsumoto et al. |
| 2010/0178512 A1 | 7/2010 | Giesenberg et al. |
| 2011/0081643 A1 | 4/2011 | Fournier-Bidoz et al. |
| 2013/0183246 A1 | 7/2013 | Wang et al. |

FOREIGN PATENT DOCUMENTS

| | | |
|---|---|---|
| CN | 101177543 A | 5/2008 |
| FR | 2921380 A1 | 9/2007 |

(Continued)

OTHER PUBLICATIONS

International Search Report and Written Opinion dated Jan. 31, 2013.

(Continued)

*Primary Examiner* — Ana Woodward (74) *Attorney, Agent, or Firm* — Thomas Horstemeyer, LLP (57) ABSTRACT

An embodiment of the present disclosure can include a compound, a structure bonded to the compound, and the like. In an embodiment, the compound can be a linker between an agent and a structure, where the agent can be a dye or a pigment and the structure can be a fiber, hair, or another structure. In an embodiment, the compound can be a linker between an agent and a structure, where the agent can be a fluorinated compound and the structure can be a counter top, metal, or the like.

19 Claims, 4 Drawing Sheets

(56) References Cited

FOREIGN PATENT DOCUMENTS

| FR | 2920781 A1 | 3/2009 |
|---|---|---|
| JP | 2005200553 A1 | 7/2005 |
| WO | 2010096444 A2 | 8/2010 |

OTHER PUBLICATIONS

Office Action in related Chinese Application No. 201080008259.0 dated Jun. 18, 2013.

Extended European Search Report dated Oct. 18, 2013.

International Search Report and Written Opinion dated Sep. 16, 2010.

Goyal; Nanoscale Approaches for Biomolecule Separtion and Detection. Master in Science in Biomedical Engineering Requirement—Graduate School of the University of Texas at Arlington. Dec. 2009.

Dendukuri, et al.; The Synthesis and Assembly of Polymeric Microparticles Using Microfluidics. Advanced Review. vol. 21, 2009. 2009 WILEY-VCH Verlag GmbH & Co. KGaA, Weinheim pp. 4071-4086.

Yuan, et al.; Large scale manufacture of magnetic polymer particles using membranes and microfluidic devices. China Particuology. vol. 5, 2007. pp. 26-42.

Chen, et al., Microfluidic Assembly of Magnetic Hydrogel Particles with Uniformly Anisotropic Structure. Advanced Review. vol. 21, 2009. 2009 WILEY-VCH Verlag GmbH & Co. KGaA, Weinheim pp. 3201-3204.

Hwang, et al., Microfluidic-based synthesis of non-spherical magnetic hydrogel microparticles. Lab on a Chip. vol. 8, 2008. The Royal Society of Chemistry 2008 pp. 1640-1647.

Shum, et al.; Droplet Microfluidics for Fabrication of Non-Spherical Particles. Macromolecular Rapid Communications. vol. 32, 2010. 2010 WILEY-VCH Verlag GmbH & Co. KGaA, Weinheim. pp. 108-118.

Wang, et al.; Fabrication of Monodisperse Toroidal Particles by Polymer Solidification in Microfluidics. ChemPhysChem. vol. 10, 2009. 2009 WILEY-VCH Verlag GmbH & Co. KGaA, Weinheim. pp. 641-645.

Examination Report on related New Zealand Application No. 602911 dated Jun. 18, 2013.

International Preliminary Report on Patentability dated Nov. 8, 2012.

International Search Report and Written Opinion dated Jan. 19, 2012.

* cited by examiner

PERMANENT ATTACHMENT OF AGENTS TO SURFACES CONTAINING C—H FUNCTIONALITY

CROSS REFERENCE TO RELATED APPLICATION

This application is the 35 U.S.C. §371 national stage of PCT application having serial number PCT/US2012/046400, filed on Jul. 12, 2012. This application also claims priority to U.S. provisional application entitled "PERMANENT ATTACHMENT OF PIGMENTS AND DYES TO SURFACES CONTAINING C—H FUNCTIONALITY," having Ser. No. 61/508,438 filed on Jul. 15, 2011, which is entirely incorporated herein by reference.

BACKGROUND

Covalent attachment of dyes and pigments to structures such as fabrics and hair can be challenging. Thus, solutions for attaching dyes and pigments to structures are actively being pursued.

SUMMARY

An embodiment of the present disclosure can include a compound, a structure bonded to the compound, and the like. In an embodiment, the compound can be a linker between an agent and a structure, where the agent can be a dye or a pigment and the structure can be a fiber, hair, or another structure. In an embodiment, the compound can be a linker between an agent and a structure, where the agent can be a fluorinated compound and the structure can be a counter top, metal, or the like.

An embodiment of the compound, among others, includes: R1-(C=O)—R2-X—W, where R1 and R2 are independently selected from the group consisting of: a substituted or unsubstituted aliphatic group, a substituted or unsubstituted aryl group, and a substituted or unsubstituted heteroaryl group; X is selected from the group consisting of: O, NR3, a substituted or unsubstituted alkyl group, a S group, a substituted or unsubstituted aryl group, and a substituted or unsubstituted heteroaryl group; wherein R3 is selected from the group consisting of: a substituted or unsubstituted aliphatic group, a substituted or unsubstituted aryl group, and a substituted or unsubstituted heteroaryl group; and wherein W is a pigment or a dye.

An embodiment of the article, among others, includes: R1-(C(Struc)OH)—R2-X—W, where R1 and R2 are independently selected from the group consisting of: a substituted or unsubstituted aliphatic group, a substituted or unsubstituted aryl group, and a substituted or unsubstituted heteroaryl group; X is selected from the group consisting of: O, NR3, a substituted or unsubstituted alkyl group, a S group, a substituted or unsubstituted aryl group, and a substituted or unsubstituted heteroaryl group; wherein R3 is selected from the group consisting of: a substituted or unsubstituted aliphatic group, a substituted or unsubstituted aryl group, and a substituted or unsubstituted heteroaryl group; wherein W is a pigment or a dye; and wherein Struc is a structure having C—H functionality.

An embodiment of the compound, among others, includes: R1-(C=O)—R2-X—W, where R1 and R2 are independently selected from the group consisting of: a substituted or unsubstituted aliphatic group, a substituted or unsubstituted aryl group, and a substituted or unsubstituted heteroaryl group; X is selected from the group consisting of: O, NR3, a substituted or unsubstituted alkyl group, a S group, a substituted or unsubstituted aryl group, and a substituted or unsubstituted heteroaryl group; wherein R3 is selected from the group consisting of: a substituted or unsubstituted aliphatic group, a substituted or unsubstituted aryl group, and a substituted or unsubstituted heteroaryl group; and wherein W is a fluorinated group.

An embodiment of the article, among others, includes: R1-(C(Struc)OH)—R2-X—W, where R1 and R2 are independently selected from the group consisting of: a substituted or unsubstituted aliphatic group, a substituted or unsubstituted aryl group, and a substituted or unsubstituted heteroaryl group; X is selected from the group consisting of: O, NR3, a substituted or unsubstituted alkyl group, a S group, a substituted or unsubstituted aryl group, and a substituted or unsubstituted heteroaryl group; wherein R3 is selected from the group consisting of: a substituted or unsubstituted aliphatic group, a substituted or unsubstituted aryl group, and a substituted or unsubstituted heteroaryl group; wherein W is a fluorinated group; and wherein the Struc is a structure having C—H functionality.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "substituted" refers to any one or more hydrogens on the designated atom that can be replaced with a selection from the indicated group, provided that the designated atom's normal valence is not exceeded, and that the substitution results in a stable compound. In an embodiment, the indicated group can include in or more halogens, aliphatic groups, and the like.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon chain and a substituted saturated aliphatic hydrocarbon chain which may be straight, branched, or cyclic, having 1 to 20 carbon atoms, where the stated range of carbon atoms includes each intervening integer individually, as well as sub-ranges. Examples of alkyl groups include, but are not limited to, methyl, ethyl, i-propyl, n-propyl, n-butyl, t-butyl, pentyl, hexyl, septyl, octyl, nonyl, decyl, and the like. The substitution can be with a halogen, for example.

As used herein, "alkenyl" or "alkenyl group" refers to an aliphatic hydrocarbon which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "alkynyl" refers to straight or branched chain hydrocarbon groups, containing at least one triple carbon to carbon bond having 2 to 20 carbon atoms, wherein the stated range of carbon atoms includes each intervening integer individually, as well as sub-ranges. An alkynyl group can be optionally substituted, unless stated otherwise, with one or more groups.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl group in which one or more hydrogens are substituted by halogen radicals. Examples of haloalkyl include, but are not limited to, trifluoromethyl, trichloromethyl, pentafluoroethyl, and pentachloroethyl.

As used herein, the term "fiber" refers to filamentous material that can be used in fabric and yarn as well as textile fabrication. One or more fibers can be used to produce a fabric or yarn. Fibers include, without limitation, materials such as cellulose, fibers of animal origin (e.g., alpaca, angora, wool and vicuna), hemicellulose, lignin, polyesters, polyamides, rayon, modacrylic, aramids, polyacetates, polyxanthates, acrylics and acrylonitriles, polyvinyls and functionalized derivatives, polyvinylidenes, PTFE, latex, polystyrene-butadiene, polyethylene, polyacetylene, polycarbonates, polyethers and derivatives, polyurethane-polyurea copolymers, polybenzimidazoles, silk, lyocell, carbon fibers, polyphenylene sulfides, polypropylene, polylactides, polyglycolids, cellophane, polycaprolactone, "M5" (poly{diimidazo pyridinylene (dihydroxy) phenylene}), melamine-formadehyde, plastarch, PPOs (e.g., Zylon®), polyolefins, and polyurethane.

The term "textile article" can include garments, fabrics, carpets, apparel, furniture coverings, drapes, upholstery, bedding, automotive seat covers, fishing nets, rope, articles including fibers (e.g., natural fibers, synthetic fibers, and combinations thereof), articles including yarn (e.g., natural fibers, synthetic fibers, and combinations thereof), and the like.

Discussion

An embodiment of the present disclosure includes a compound, a structure bonded to the compound, and the like. In an embodiment, the compound can be a linker between an agent and a structure, where the agent can be a dye or a pigment and the structure can be a fiber, hair, or another structure. In an embodiment, the compound can be a linker between an agent and a structure, where the agent can be a fluorinated compound and the structure can be a counter top, metal, or the like.

An embodiment of the present disclosure includes a compound (linker) such as that shown below. In an embodiment, the compound can covalently bond to a structure or a surface having C—H functionality, while also bonding to a dye, pigment, and/or a fluorinated compound. In an embodiment, the surface or structure inherently has C—H functionality. In this regard, an agent, such as a pigment or dye, can be attached to a surface or structure having C—H functionality. In an embodiment, the surface or structure can be coated with a film or material (functionalized layer) that has C—H functionality or otherwise modified to have C—H functionality.

In an embodiment, the compound can be used to bind to a surface or structure having C—H functionality such as a polypropylene fiber, a polyethylene fiber, a polyester fiber, a polyamide fiber, an aramid fiber, a natural fiber, as well as natural surfaces, or another surface or structure having C—H functionality. In addition, the compound can be used to bind to a surface or structure having C—H functionality such as textile articles, counters, processing equipment, utensils, food packaging materials, metals, plastic structures, medical instruments, medical implants, diapers, leathers, flooring, and the like, so that a dye or pigment can be attached to these.

In an embodiment, the compound can have the following formula: R1-(C=O)—R2-X—W. In an embodiment, R1 and R2 are independently selected from aliphatic group (substituted or unsubstituted and/or linear, branched, or cyclic) (e.g., alkyl, alkenyl, alkynyl), an aryl group (substituted or unsubstituted), or a heteroaryl group (substituted or unsubstituted). In an embodiment, at least one of R1 and R2 is a substituted or unsubstituted aryl group. In an embodiment, at least one of R1 and R2 is a substituted or unsubstituted phenyl group.

In an embodiment, X can be, an aliphatic group (substituted or unsubstituted and/or linear, branched, or cyclic) (e.g., alkyl, alkenyl, alkynyl), an aryl group (substituted or unsubstituted), a heteroaryl group (substituted or unsubstituted), an oxygen group (e.g., O—R1'), an amine group (e.g., primary, secondary, or tertiary, where each can have an appropriate number of R1' groups that are independently selected), a sulfur group (e.g., S—R1', wherein one or more R1 can be present), and the like. In an embodiment, R1' can be an aliphatic group (substituted or unsubstituted and/or linear, branched or cyclic), an aromatic group (substituted or unsubstituted), an aryl group (substituted or unsubstituted), a heteroaryl group (substituted or unsubstituted), and the like.

In an embodiment, W can be a dye, a pigment, or a fluorinated compound.

In an embodiment, the compound functions to at least undergo a photochemical change to covalently bond with a surface or a layer on the surface of a structure having a C—H group. In an embodiment, the composition is covalently bonded via the interaction of the polymer with a UV light (e.g., about 250 nm to 500 nm or about 340 to 370 nm) that causes a C—C bond to form between the polymer and the surface or a layer on the surface having the C—H group. The UV light can be generated from a UV light source such as those known in the art.

In an embodiment, the compound can include an aryl ketone (about 340 to 400 nm), an aryl azide group (about 250 to 450 nm or about 350 to 375 nm), a diazirine group (about 340 to 375 nm), and the polymer can include a combination of these groups. In an embodiment, the linker can include alkylarylketones and diarylketones bearing at least one condensed ring system substituent such as naphtyl and anthracenyl (See Example IV). In an embodiment, the aryl ketone group can include benzophenone (about 340 to 380 nm), acetophenone (about 340 to 400 nm), a naphthylmethylketone (about 320 to 380 nm), a dinaphthylketone (about 310 to 380 nm), a dinaphtylketone derivative (about 320 to 420 nm), or derivatives of each of these. In an embodiment, the linker is a benzophenone group. In an embodiment, the aryl azide group can include phenyl azide, alkyl substituted phenyl azide, halogen substituted phenyl azide, or derivatives of each of these. In an embodiment, the diazirine group can include 3,3 dialkyl diazirine (e.g., 3,3 dimethyl diazirine, 3,3 diethyl diazirine), 3,3 diaryl diazirine (e.g., 3,3 diphenyl diazirine), 3-alkyl 3-aryl diazirine, (e.g., 3-methyl-3-phenyl diazirine), or derivatives of each of these.

As noted above, the compound can be covalently bonded to a structure. In an embodiment, the article including the compound can be represented as: R1-(C(Struc)OH)—R2-X—W. R1, R2, X, and W are defined herein. "Struc" can include structures defined herein that include C—H functionality.

As noted above, the compound can be attached to pigments and dyes. Although not intending to be limited to the dyes and pigments described herein, the following presents some illustrative examples of dyes and pigments.

Organic pigments are varied in their structures and functionalities. However, the most common pigments are derivatives of aromatic amines, quinones, azo compounds, or quinonediimines. The structures of some common pigments/dyes appear below, without any intent to limit the applicability of this technology to the pigments described herein:

Morindone [CAS 478-29-5], a red compound that requires a mordant and may yield different shades of red depending on the mordant used.

Alizarin [CAS 72-48-0], also a red dye, frequently used in the textile industry.

Anthrapurpurin [CAS 602-65-3], a purple dye

Carminic acid [CAS 1260-17-9], a naturally occurring dye with a crimson color 1,4-Diamino-2,3,dihudroanthraquinone [CAS81-63-0], also known as Disperse Red 9 or Solvent Violet 47, an important industrial dye.

1,4-diamino-2-methoxy anthraquinone, [CAS 2872-48-2], also known as Disperse Red 11 or C.I. 62015 is a common red dye.

1,4-bis(butylamino) anthraquinone [CAS 17354-14-2], also called Oil Blue 35, Solvent Blue 35, Blue 2N, Blue B, Oil Blue B, 1,4-bis(butylamino) anthraquinone and CI 61554 is a deep blue dye

Lawsone (2-hydroxy-1,4-naphthoquinone), also known as hennotannic acid [CAS 83-72-7] is a naturally occurring dye derived from the henna plant, which renders skin and hair surfaces with a tint ranging from orange to brown. It is also used a as natural UV filter in sunless tanning sunscreens.

Pararosaniline (Basic red 9; C.I. 42500; [CAS 569-61-9] is a magenta/red dye. When modified by successive methylation of the amino groups, it yields several other important pigments, as below

Methyl violet

Crystal violet (Methyl violet 10B; [548-62-9]

Methyl green

Methyl violet 2B [8004-87-3]

Methylene blue [61-73-4] is an example of a blue pigment used only in temporary staining and normally not used in the textile industry, but that can be permanently attached to surfaces using the chemistry described herein.

Carotenes, which are yellow-orange pigments

Bixin (annatto) is a natural pigment with an intense orange color, normally used in the food industry, and not in the textile industry. As with other dyes/pigments, it can be permanently affixed onto C—OH containing surfaces through the use of this technology.

Other common dyes include:

Brilliant Green[633-03-04]

Light Green SF yellowish (FD&C Green #2, Pencil Green CF) [5141-20-8]

Tartrazine, E102, FD&C Yellow 5 [1934-21-0], which is a lemon-yellow dye

Quinoline yellow, C.I. 47005, Food Yellow 13 CAS [8004-92-0]

Quinoline yellow SS [8003-22-3]

As mentioned above, W can be a fluorinated compound such a fluorinated aliphatic group (substituted or unsubstituted and/or linear, branched, or cyclic) (e.g., alkyl, alkenyl, alkynyl), a fluorinated aryl group (substituted or unsubstituted), a fluorinated heteroaryl group (substituted or unsubstituted), a fluorinated oxygen group (e.g., O—R1'), a fluorinated amine group (e.g., primary, secondary, or tertiary, where each can have an appropriate number of R1' groups that are independently selected), a fluorinated sulfur group (e.g., S—R1', wherein one or more R1' can be present), and the like.

In an embodiment, the fluorinated compound can be a fluoropolymer. In addition, one or both of R1 and R2 can be fluorinated (e.g., a fluorinated aryl group). The term "fluoropolymer" can include a polymer having at least one fluorine-containing monomer and can be a homopolymer, copolymer, and terpolymer. Embodiments of the fluoropolymer can include polymers such as, but not limited to, polytetrafluoroethylene (PTFE), fluorinated ethylene-propylene (FEP), perfluoroalkoxy polymer resin (PFA), polychlorotrifluoroethylene (PCTFE), polytrifluoroethylene, polyvinylidene fluoride (PVDF), polyvinyl fluoride (PVF), tetrafluoroethylene-ethylene copolymer resin (ETFE), fluoroethylene propylene ether resin (EPE), copolymers of each, terpolymers of each, and the like. In an embodiment, the fluoropolymer can be PTFE, PFA, FEP, copolymers of each, terpolymers of each, or a combination thereof, where PTFE, PFA, and FEP refer to a chemical that can be used to form Teflon®. In an embodiment, the fluoropolymer is PTFE.

As used herein, the term "PTFE" includes polytetrafluoroethylene as well as its derivatives, composites and copolymers thereof, wherein the bulk of the copolymer material can be polytetrafluoroethylene, including copolymers of tetrafluoroethylene and hexafluoro(propyl vinyl ether), copolymers of tetrafluoroethylene and perfluoro-2,2-dimethyl-1,3-dioxole, and copolymers of tetrafluoroethylene and vinyl fluoride, poly(vinyl fluoride), poly(vinylidene fluoride), polychlorotrifluoroethylene, vinyl fluoride/vinylidene fluoride copolymer, vinylidene fluoride/hexafluoroethylene copolymer, perfluoroalkoxy polymer resin (PFA), and/or fluorinated ethylene-propylene (FEP). Where the term "PTFE" is used herein to describe polytetrafluoroethylene that is copolymerized with one of the above-named polymers, it is contemplated that the actual polytetrafluoroethylene content in the copolymer can be about 80% by weight, or higher, although lower amounts are also contemplated depending on the desired properties of the resulting compound.

EXAMPLE

Now having described the embodiments of the disclosure, in general, the examples describe some additional embodiments. While embodiments of the present disclosure are described in connection with the example and the corresponding text and figures, there is no intent to limit embodi- ments of the disclosure to these descriptions. On the contrary, the intent is to cover all alternatives, modifications, and equivalents included within the spirit and scope of embodiments of the present disclosure.

Example 1

Permanent Affixation of Pigments and Dyes onto Surfaces

Figure 1:
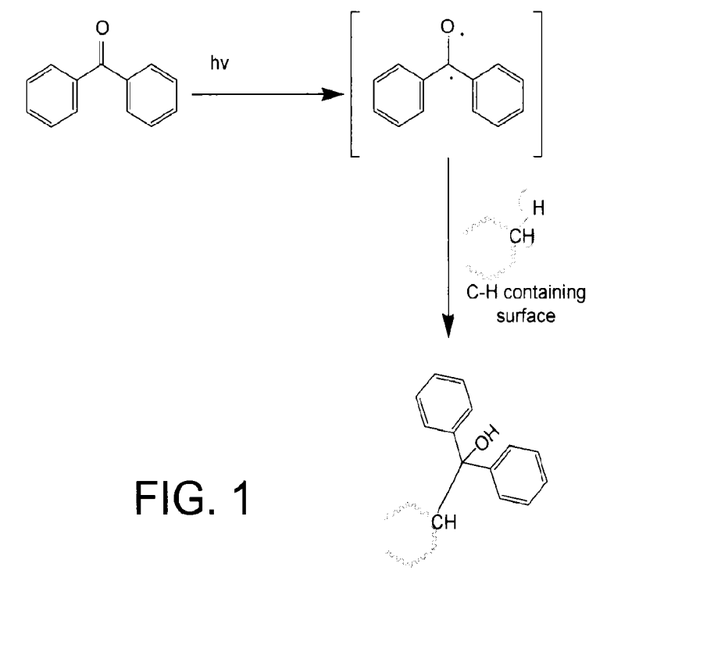
FIG. 1 illustrates an embodiment of a method used for activation of C—H functionality.

The method used herein benefits from the activation of C—H functionality on surfaces by radicals such as dephenylketyl ([Ø$_2$C—O].) to yield an ether through the insertion of the dephenylketyl group into the CH bond (FIG. 1).

A ligating agent (linker) for which the structure (A) is shown below, can be used to form a derivative of a dye (e.g., (B) and (C) below; R=phenyl and X=CH$_2$)) which is then permanently attached to a substrate by the light-initiated insertion reaction described in FIG. 2 (D) (e.g., using polyethylene as substrate).

(A)

R=alkyl, aryl. Preferably, at least one of R is an aryl group
X=O, NR, (CH2)n, S, aryl (B) Morindone derivative (C) Methylene Blue Derivative

Figure 2:
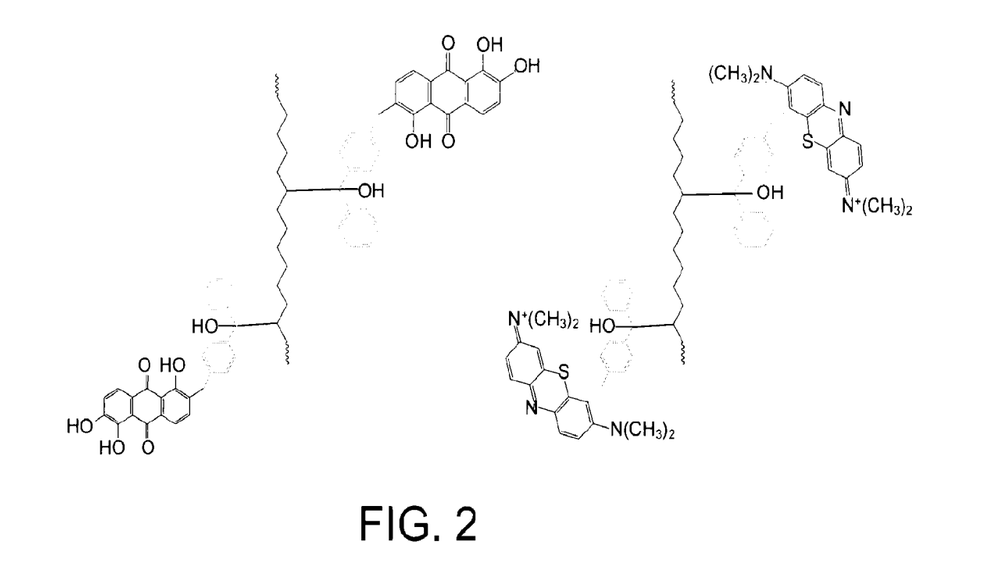
FIG. 2 illustrates embodiments of the present disclosure.

FIG. 2 illustrates (D) morindone and methylene blue permanently attached to polyethylene.

It will be apparent for someone skilled in the art that the linker (A) may be attached to any of the pigments described herein and the derivatives thereof and reacted at a surface C—H group, through light activation, to covalently attach pigments to those surfaces.

Surfaces of the present disclosure can be other polymeric surfaces, such as for instance, and without intending to be limiting, polyesters, polyamides, aramids, cellulose (some or which are shown below). In fact, any surface with a C—H bond is amenable to undergo modification by this method.

Polyamide

Polyester

Aramid

Cellulose

Example 2

Permanent Attachment of Dyes to Hair

The most popular way to achieve permanent hair coloring is through the use of oxidation dyes. The ingredients include 1,4-diaminobenzene (historically) or 2,5-diaminotoluene (currently), a coupling agent, and an oxidant. The process is typically performed under basic conditions.

The mechanism of oxidation dyes involves three steps: 1) Oxidation of 1,4-diaminobenzene derivative to the quinone state. 2) Reaction of this diimine with a coupler (more detail below). 3) Oxidation of the resulting compound to give the final dye. The preparation (dye precursors) is in the leuco (colorless) form. Oxidizing agents are usually hydrogen peroxide, and the alkaline environment is usually provided by ammonia. The combination of hydrogen peroxide and the primary intermediate causes the natural hair to be lightened, which provides a blank canvas for the dye. Ammonia opens the hair shaft so that the dye can actually bond with the hair, and ammonia speeds up the reaction of the dye with the hair.

Various combinations of primary intermediates and couplers provide a spectrum of shades of hair colors. The primary intermediates are aromatic para compounds, such as 1,4-diaminobenzene or 4-aminophenol. The couplers are meta-substituted derivatives of aniline. They come in three major classes based on the color that they produce when they react with the primary intermediate.

Couplers are chemical compounds that define the color of the hair dye. Shown above are three red couplers (A,B,C), two yellow-green couplers (D,E) and a blue coupler (F).

Blue couplers include 1,3-diaminobenzene and its derivatives.

Red couplers include phenols and naphthols, such as 3-aminophenol (CAS#591-27-5), 5-amino-2-methylphenol (CAS#2835-95-2) and 1-naphthol (CAS#90-15-3). The combination of 2,5-diaminotoluene with the coupler 3-aminophenol gives a magenta-brown dye, while the combination of 2,5-diaminotoluene with the coupler 1-naphthol gives a purple dye.

Yellow-green couplers include resorcinol, 4-chlororesorcinol, and benzodioxoles. These compounds produce broadband absorption when they react to form dyes, allowing for more natural-looking hair colors. The combination of 2,5-diaminotoluene with the coupler resorcinol gives a greenish brown dye.

The first step shows the oxidation of p-phenylenediamine to the quinonediimine ($C_6H_4(NH)_2$):

This species exists in equilibrium with the monoprotonated form ($C_6H_4(NH)(NH_2)^+$) (not shown). The second step involves the attack of this quinonediimine on the coupler. In organic chemistry, this reaction is called electrophilic aromatic substitution:

In the third and final step, the product from the quinonediimine-coupler reaction oxidizes to the final hair dye.

The resulting hair dye is also much larger than the precursor molecules, which causes the dye to bond to the hair.

Figure 3:
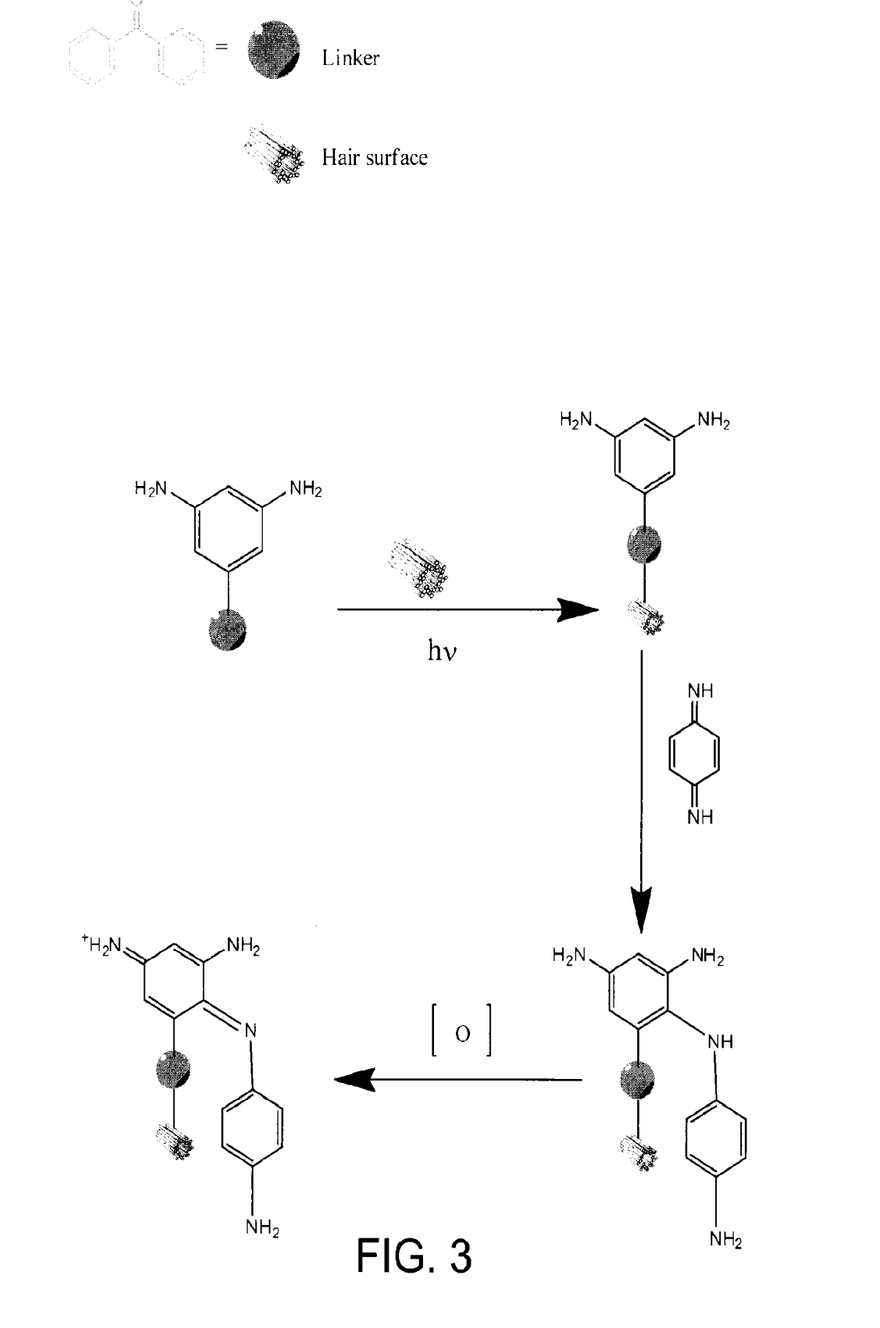
FIG. 3 illustrates an embodiment of a method used for activation of C—H functionality.

One embodiment of the present disclosure permits the permanent coloring of hair (especially bleached hair), using a strategy that is similar to that used. The linker (A) above may be used to affix the coupler to hair, following the reaction with quinonediimine and oxidation (FIG. 3).

Example 3

Modification of the Hydrophilicity and Polarity of Surfaces

Modification of the hydrophilic character of surfaces is process of industrial importance especially in the manufacture of textiles, glasses, certain metal surfaces. Turning a surface hydrophobic, or coating an already hydrophobic surface with a secondary layer of hydrophobic material, is a key component in the manufacture of textiles capable to prevent staining, self-cleaning glass, impermeabilization of outdoor gear (military, sports), corrosion prevention of metals exposed to humidity, etc.

Hydrophobic coatings can be made of, for instance, polyethylene. However, coating with polyfluoro polymers is often preferred, given their inertia toward solvents, acids, bases, exposure to sunlight and, more importantly, very low surface drag coefficient. For instance, poly (fluorinated ethylepropilene)—a copolymer of $F_2C\!=\!CF_2$ and $CF_3\!-\!CF_2\!=\!CF_2\!-$ is used as coatings on glass panels rendering these "self-cleaning". Coating with fluorocarbon compounds is also important to render materials inert to fire. An embodiment of the present disclosure is suited to promote the attachment of monomeric and polymeric materials onto surfaces containing C—H bonds, through insertion of dephenylketyl as discussed above.

Figure 4:
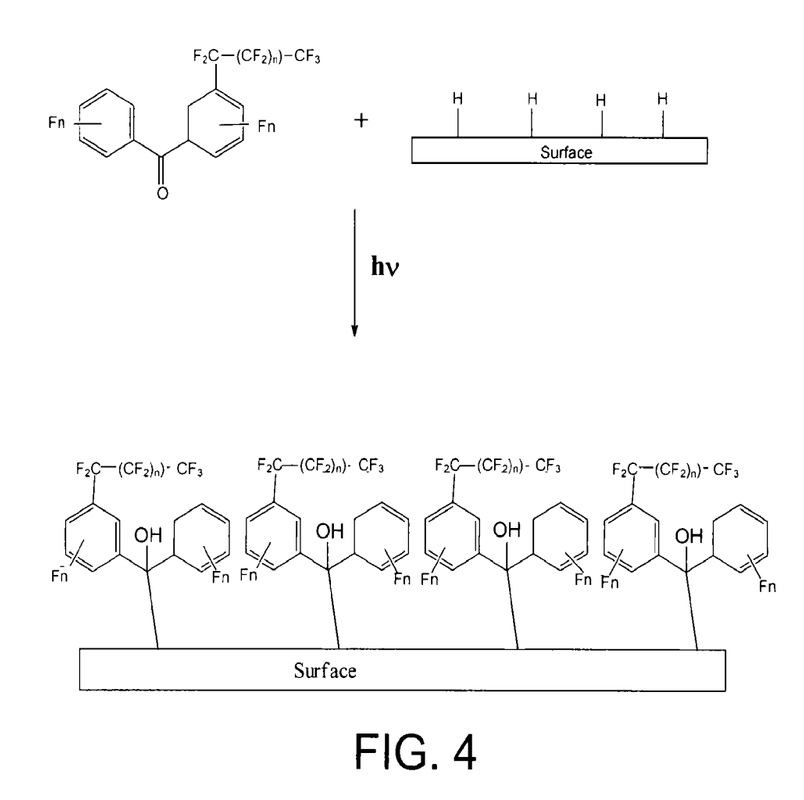
FIG. 4 illustrates an embodiment of a method used for activation of C—H functionality.
Figure 5:
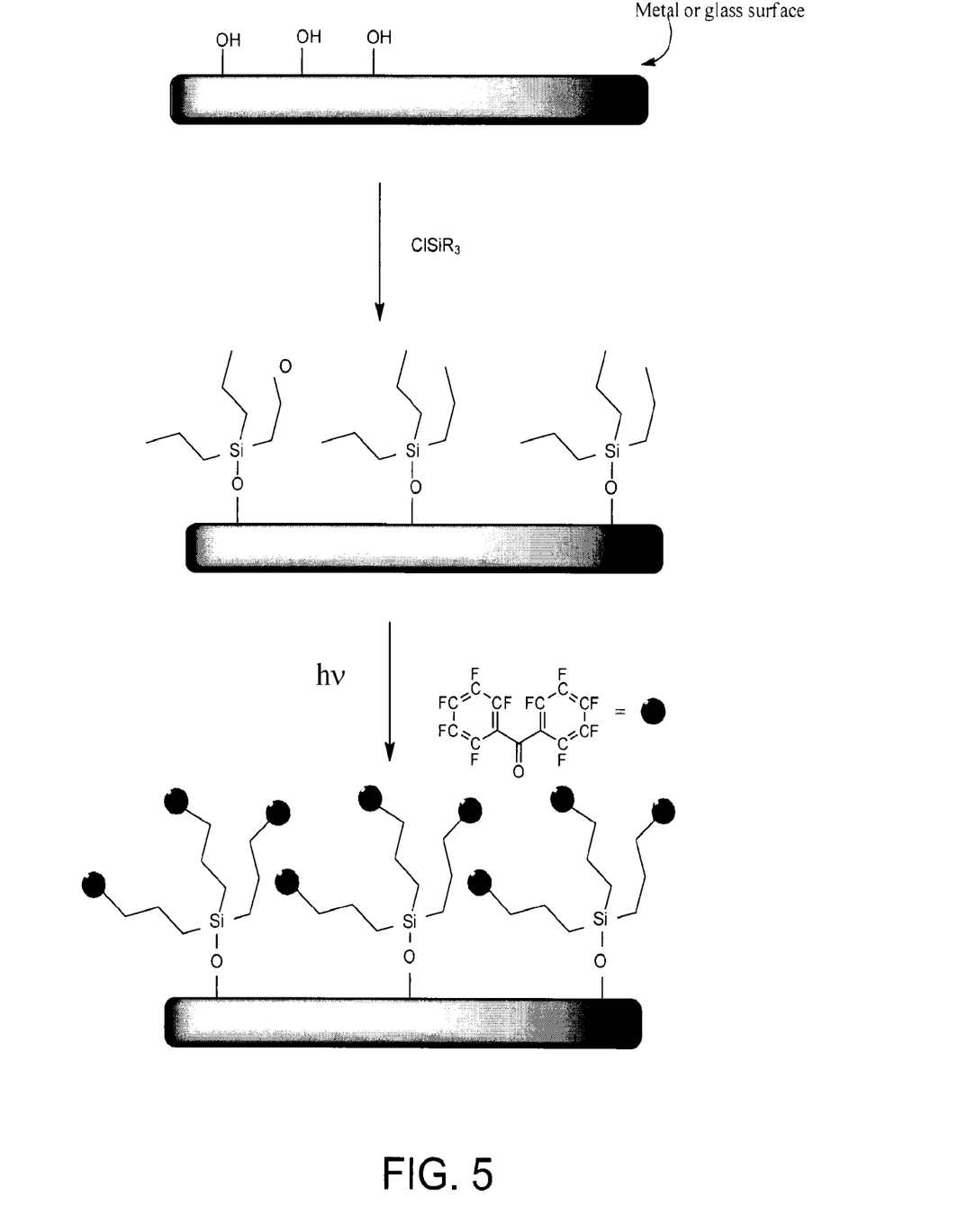
FIG. 5 illustrates an embodiment of a method used for activation of C—H functionality.

For this purpose, the materials to be attached onto a substrate are derivatized with the linker (A) and the resulting compound is sprayed onto a surface which is then exposed to UV or direct sunlight:

In an embodiment, the linkers could also be, for example, without intending to be limiting:

Glass and metal surfaces can also be modified according to the method of the present disclosure, through the use of the OH groups present in the termination layer of these materials. That termination layer can be modified, for instance, through reaction with silanes, to provide for a second, C—H rich layer, which is then modified according to the method of the of the present disclosure, as shown in FIGS. 4 and 5.

The invention claimed is:

1. A compound comprising:
R1-(C=O)—R2-X—W, where R1 and R2 are independently selected from the group consisting of: a substituted or unsubstituted aliphatic group, a substituted or unsubstituted aryl group, and a substituted or unsubstituted heteroaryl group; X is selected from the group consisting of: O, NR3, a substituted or unsubstituted alkyl group, a S group, a substituted or unsubstituted aryl group, and a substituted or unsubstituted heteroaryl group; wherein R3 is selected from the group consisting of: a substituted or unsubstituted aliphatic group, a substituted or unsubstituted aryl group, and a substituted or unsubstituted heteroaryl group; and wherein W is a pigment or a dye, wherein substituted includes substitution of one or more H independently with a halogen or an aliphatic group.

2. The compound of claim 1, wherein one of R1 and R2 is a substituted or unsubstituted aryl group.

3. The compound of claim 2, wherein X is an alkyl group.

4. The compound of claim 2, wherein X is an aryl group.

5. The compound of claim 2, wherein X is a heteroaryl group.

6. The compound of claim 2, wherein X is O.

7. The compound of claim 1, wherein both of R1 and R2 is a substituted or unsubstituted aryl group.

8. The compound of claim 7, wherein X is an alkyl group.

9. The compound of claim 7, wherein X is an aryl group.

10. The compound of claim 7, wherein X is a heteroaryl group.

11. The compound of claim 7, wherein X is O.

12. The compound of claim 1, wherein one of R1 and R2 is a substituted or unsubstituted phenyl group.

13. The compound of claim 12, wherein X is an alkyl group.

14. The compound of claim 12, wherein X is O.

15. The compound of claim 1, wherein both of R1 and R2 is a substituted or unsubstituted phenyl group.

16. The compound of claim 1, wherein X is an alkyl group.

17. The compound of claim 1, wherein X is an aryl group.

18. The compound of claim 1, wherein X is a heteroaryl group.

19. The compound of claim 1, wherein X is O.

* * * * *